(12) United States Patent
Wingren

(10) Patent No.: US 9,655,206 B2
(45) Date of Patent: May 16, 2017

(54) LIGHT CONTROL SYSTEM

(71) Applicant: BrainLit AB, Malmö (SE)

(72) Inventor: Tord Wingren, Malmö (SE)

(73) Assignee: BrainLit AB, Malmö (SE)

( * ) Notice: Subject to any disclaimer, the term of this patent is extended or adjusted under 35 U.S.C. 154(b) by 0 days.

(21) Appl. No.: 15/087,289

(22) Filed: Mar. 31, 2016

(65) Prior Publication Data
US 2016/0219675 A1    Jul. 28, 2016

Related U.S. Application Data

(63) Continuation of application No. 14/385,955, filed as application No. PCT/SE2013/050288 on Mar. 15, 2013, now Pat. No. 9,313,860.

(60) Provisional application No. 61/612,468, filed on Mar. 19, 2012.

(51) Int. Cl.
| H05B 37/02 | (2006.01) |
| A61N 5/06 | (2006.01) |
| A61M 21/02 | (2006.01) |
| A61M 21/00 | (2006.01) |

(52) U.S. Cl.
CPC ......... *H05B 37/0218* (2013.01); *A61M 21/00* (2013.01); *A61N 5/06* (2013.01); *A61N 5/0618* (2013.01); *H05B 37/0227* (2013.01); *H05B 37/0272* (2013.01); *A61M 21/02* (2013.01); *A61M 2021/0044* (2013.01); *A61M 2205/3306* (2013.01); *A61M 2205/3561* (2013.01); *A61M 2205/3592* (2013.01); *A61M 2205/50* (2013.01); *A61N 2005/0626* (2013.01); *Y02B 20/46* (2013.01)

(58) Field of Classification Search
CPC ............ H05B 37/0218; H05B 37/0227; H05B 37/0272; A61M 21/00
USPC ................................................. 315/148–158
See application file for complete search history.

(56) References Cited

U.S. PATENT DOCUMENTS

| 2005/0015122 A1 | 1/2005 | Mott et al. | |
| 2010/0301776 A1* | 12/2010 | Feri ...................... | H05B 37/029 315/312 |
| 2011/0160881 A1* | 6/2011 | Grey ...................... | G06Q 10/06 700/90 |
| 2012/0169238 A1 | 7/2012 | Lenderink | |

(Continued)

FOREIGN PATENT DOCUMENTS

| EP | 2156861 A1 | 2/2010 |
| WO | WO-2007141674 A1 | 12/2007 |
| WO | WO-2010079388 A1 | 7/2010 |

(Continued)

OTHER PUBLICATIONS

Bengtsson, Rune, "International Search Report," prepared for PCT/SE2013/050288, as mailed Jul. 16, 2013, three pages.

*Primary Examiner* — Douglas W Owens
*Assistant Examiner* — Jonathan G Cooper
(74) *Attorney, Agent, or Firm* — Winstead PC

(57) ABSTRACT

A light control system having a central control engine, at least one light sensor, and at least one light source. The central control engine is configured to receive illumination data from the light sensor. The light data represents an actual light profile. The central control engine is configured to retrieve a target light profile for a user and adjust an illumination of the light control system based on the target light profile for the individual user.

18 Claims, 2 Drawing Sheets

(56) References Cited

U.S. PATENT DOCUMENTS

2012/0169249 A1\* 7/2012 Loveland .......... H05B 37/0245
　　　　　　　　　　　　　　　　　　　　　　　　315/291

FOREIGN PATENT DOCUMENTS

| WO | WO-2011089539 A1 | 7/2011 |
| WO | WO-2011094742 A2 | 8/2011 |
| WO | WO2012023488 * | 2/2012 |
| WO | WO-2012111534 A1 | 8/2012 |
| WO | WO-2014013376 A1 | 1/2014 |

\* cited by examiner

LIGHT CONTROL SYSTEM

This application is a continuation of U.S. patent application Ser. No. 14/385,955, which entered the national stage in the U.S. on Sep. 17, 2014. U.S. patent application Ser. No. 14/385,955 is a national-stage application of PCT/SE2013/050288, filed Mar. 15, 2013. PCT/SE2013/050288 claims priority to U.S. Provisional Patent Application No. 61/612,468, filed Mar. 19, 2012. U.S. patent application Ser. No. 14/385,955, PCT/SE2013/050288, and U.S. Provisional Patent Application No. 61/612,468 are incorporated herein by reference.

TECHNICAL FIELD

This application relates to a system and an apparatus for improved lighting, and in particular to a system and an apparatus for improved lighting accommodating for an individual's lighting needs.

BACKGROUND

It has become known that many people have different lighting needs, that is they are affected by the light in their environment in different ways and therefore have different needs when it comes to the surrounding light. Some of these needs stem from physical conditions (for example eye problems), some stem from mental conditions (for example winter depressions) and some stem from personal preference. Some also stem from task oriented requirements for a specific room (for example watching TV is best done in low light).

To illustrate further it is assumed that all sorts of life is depending on light and the quality of light, and that all individuals of species have individual need of light intensity, spectral distribution and time distribution (wavelengths, amplitudes and time distribution). Furthermore, the individual need, as will be described by the target light profile, TLP, is also believed to vary over eg. time, age, state of health, sleep, food/nutrition and medical/chemical intake.

There is thus a need for a system where an individual's needs are taken into account.

SUMMARY

It is an object of the teachings of this application to overcome the problems listed above by providing a light control system comprising a central control engine, at least one light sensor and at least one light source, wherein said central control engine is configured to: receive illumination data from the light sensor, which light data represents an actual light profile; retrieve a target light profile for a user; and adjust an illumination of the light control system based on the target light profile for the individual user.

The inventors of the present invention have realized, after inventive and insightful reasoning, that by adapting measuring the light exposure of an individual and a clever arrangement of controllable light sources a light system may be controlled to accommodate an individual's needs and preferences. This is achieved in a simple manner that has the benefit of being a simple solution to a problem that has existed for a long time. The use of light sensors has existed for numerous years and the preference for certain light conditions have existed for even longer.

This document describes a light control system, LCS, that (continuously) measures and records light over time, exposed on individuals in the system which might be absorbed or/and reflected, and collects input data from distributed sensors but also individually placed (such as body placed sensors but also other sensors), and adopts the transmitted light provided by the light sources in the system to the individuals in the system, to match each individual's need.

The LCS may be distributed both in-door or out-door in multiple environments and in environments where a distribution of light sources will vary eg. where there are spots of very low or even lacking or gap of light sources (lack of controllable light sources).

A number of LCS can exist in parallel and can also co-exist with non-system enabled light or with other systems. Such LCS may be operated privately in private homes and/or by commercial light providers, CLPs, in public or work environments (for example streets, offices, stores, shopping centres, train stations, airports etc) but there may also be a mixture or combination of CLPs on local, regional, national or even international and global basis.

One implementation may be that an individual has invested in his home LCS and operates that LCS in his home, but the individual also has a subscription to a certain CLP and is therefore registered with that certain CLP. This allows the individual to roam and be part of a CLPs light network, where the CLP will give each subscriber an individually adopted light, as described herein.

One aspect of the teachings herein is to provide a light source arranged to be used on a light control system as above.

One aspect of the teachings herein is to provide a light sensor arranged to be used on a light control system as above.

Benefits brought about by a system according to the teachings herein includes, but are not limited to individual health tracking, energy tracking, bring a light experience with you to another location, share a light experience with other individuals, special light treatment cells/zones, communication through light, precision location tracking, especially in house and alarm detection and surveillance.

Other features and advantages of the disclosed embodiments will appear from the following detailed disclosure, from the attached dependent claims as well as from the drawings.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of the element, device, component, means, step, etc., unless explicitly stated otherwise.

BRIEF DESCRIPTION OF DRAWINGS

The invention will be described in further detail under reference to the accompanying drawings in which.

DETAILED DESCRIPTION

The disclosed embodiments will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout.

Figure 1:
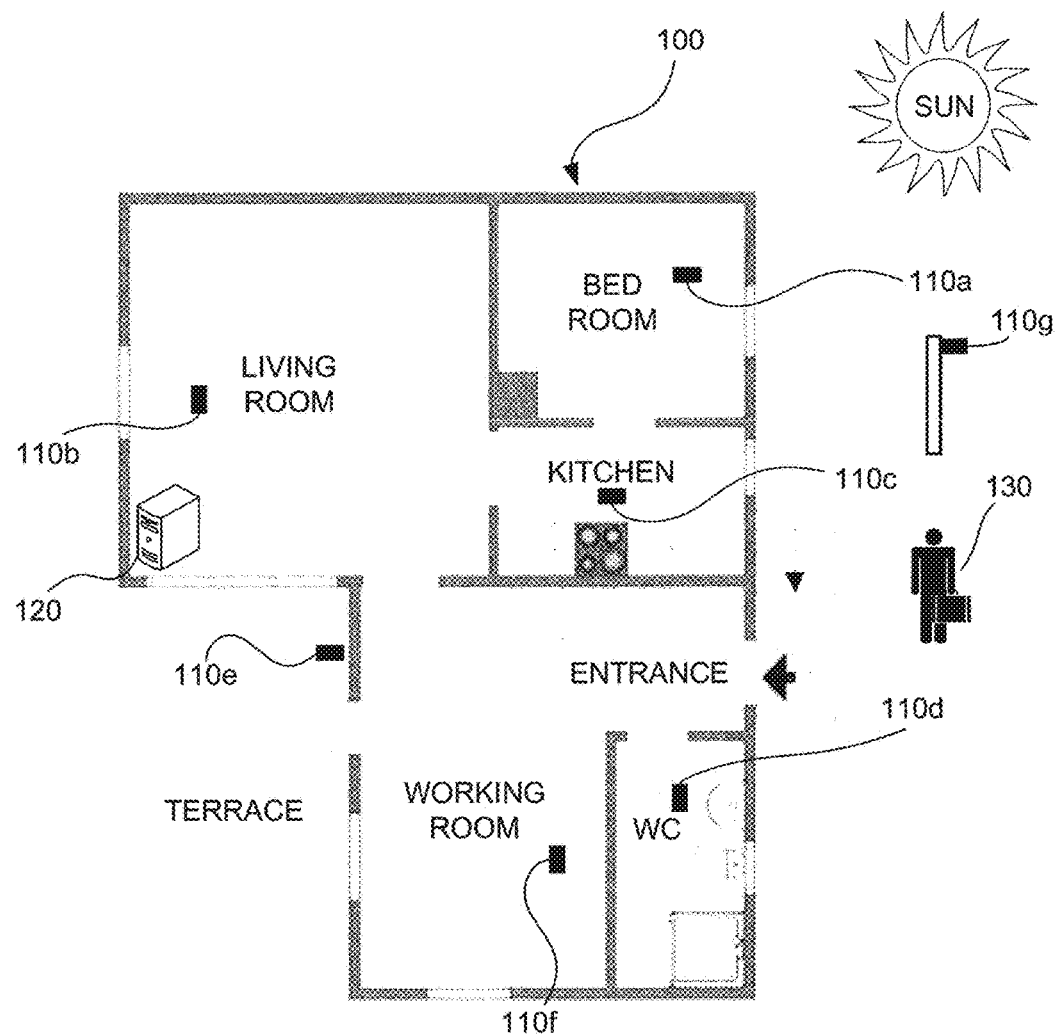
FIG. 1 shows a schematic view of a house arranged with a light control system according to one embodiment of the teachings of this application.

FIG. 1 shows a schematic view of a building 100 arranged with a Light Control System, LCS (referenced 200 in FIG. 2), according to one embodiment of the teachings herein. In FIG. 1, the LCS comprises a plurality of light sources 110 (LS). In the example of FIG. 1 there are 7 LS 110a-g. The system also comprises at least one light sensor 130. In the example of figure, the light sensor 130 is worn by an individual, but it should be noted that there may be a plurality of light sensors 130, both worn by individuals (or the same individual) as well as mounted or arranged through (inside and possibly outside) the building 100. The light sensor(s) 130 are arranged to measure an illumination level and/or a spectral density and communicate the measurement to a Central Control engine 120 that is part of the LCS and arranged to control the operation of the LCS. Likewise, the LS 110 are arranged to be controlled by the CCE 120 to adjust the illumination of the area in which the LS 110 is arranged.

Outside the house 100 is a sun, which represent ambient or surrounding light which is also to be included in the light control system. Such ambient light may be controlled through the use of blinds and such.

It should be noted that even though the description herein mostly focus on a house, a Light Control System according to the teachings herein may also be utilized in other buildings and also outdoors or a combination thereof. Outdoor light sources that may be included in the light control system include, but is not limited to, street lamps, traffic lights 110g, and light showers etc.

The CCE 120 of the LCS 200 will record all light that an individual has been exposed to over time, including sunlight, side light, reflected light etc. This recorded data will form the individual actual light profile, ALP. The CCE 120 is further configured to compare the ALP with a preferred or Target Light Profile, TLP.

In one embodiment the CCE 120 is configured to perform the light recording or measuring continuously and also at any locality, for example both indoor and outdoor, when travelling, during sleep etc. The ALP is thus updated continuously, even if the individual might be out of reach from the system LS 110. The input data from the recording may thus from time to time be recorded locally in clients, should they not have access to the CCE 120 at the time of recording. The input data will then be synchronized with the CCE 120 from time to time.

The TLP may also be adjusted dynamically. The TLP is based on many factors and may change according to these factors. Examples of factors are state of health, food intake, time of the day, sleep history, medical intake etc.

The adjustment of a TLP is effected by the CCE 120 based on a mapping engine, ME which represents known relationships between the individual factors and the desired, targeted, light need for the individual (TLP). Registration of the Individual Factor and its changes may be effected through the clients or individual sensors.

The LCS components (LS and light sensors) may also change from time to time (for example a LS may be interchanged) and the CCE 120 will recognize the new system configuration with all available light sources at any time and have the updated location data with all individual user's locations and thereby adjust the light sources 110 to continuously align each individual actual light profile, ALP, with the individual target light profile, TLP.

A light profile, such as the ALP and the TLP contains data on the amount of illumination received/to be received, at what spectrum and at what intensity. It may also comprise data on what increment or frequency the illumination should be/has been received at.

The light profile may be dependent on factors such as race, age, sex and/or health status of the user, geographical location, season, weather reports) and of course, personal preference.

The health status may relate to both physical health and mental health. An example of a mental health condition that is influenced by light is winter/darkness depressions which are often treated with light therapy.

An example of physical health status is eye problems which may render a user's eyes very sensitive to certain amounts of light.

An example of geographical conditions is for example in a ski resort where the amount of UV radiation so the LCS will compensate by reducing the UV spectra of any LSs having such spectra.

In addition, the LCS will be designed for a minimal power consumption. The LCS is configured to reduce the power consumption by for example turning the light off when there are no people in a specific room or area.

The CCE 120 may also perform a system analysis to minimize impact from great fluctuations and other light variations which could cause for example irritation, headache or other distracting mechanisms.

In one embodiment the CCE 120 is configured to continuously adapt and control the LS for the complete LCS with all individuals in the system. For individuals not registered in the system, the system will give a standard light at each location.

The CCE 120 is configured to adjust the light and the illumination level in the LCS 200 to service one user individually by adjusting the illumination based on the TLP of the individual user.

The adjustment may be based on the TLP alone, for example to always maintain a bright area where the user is visiting.

The CCE 120 may also or alternatively be arranged to take into account the light consumption already done by the individual. The light consumption is given by the ALP, which may give a current consumption or an integrated consumption. The CCE 120 is thus configured to adjust the illumination based on a difference between the ALP and the TLP.

The CCE 120 is configured to compare the ALP to the TLP and adjust the illumination accordingly. If the ALP exceeds the TLP (or a level of the ALP exceeds a level of the TLP), the illumination in the LCS 200 is decreased accordingly.

If the ALP does not reach the TLP (or a level of the ALP does not reach a level of the TLP), the illumination in the LCS 200 is increased accordingly.

The CCE 120 is configured to base the adjustment on the Mapping Engine, which may be a software module, arranged to represent the relations between a target light profile, the status or other individual factors of a user and the actual light profile, The ME also provides an indication in which manner the light or illumination should be adjusted.

The CCE 120 may also or alternatively be configured to base the adjustment of the illumination on a calendar application for determining the time available to reach a target level. If the calendar or time application indicates that an individual is likely to go to bed soon, but has not yet reached his daily quota of light, the illumination in the LCS may be increased further to make sure that the quota is reached in time.

The LCS is thus enabled to provide an individual adaptation of a light system.

The LCS 200 may also be arranged to service more than one individual, for example user 1 and user 2 having TLP1 and TLP2 respectively. To accommodate both users' TLPs the CCE 120 is configured to control the LCS according to an average of the two (or more) users' TLPs or the average of the difference between the two TLPs and the two corresponding ALPs.

However, the TLPs may be different or even conflicting. For example, if user 1 is a moody teenager he may have set his TLP1 to prefer darker light settings, whereas user 2 may have winter depressions and therefore have a TLP2 to prefer brighter settings. The two TLPs are thus conflicting in nature.

To resolve any conflicts a CCE is arranged to assign a priority to a TLP. The priority may also be assigned by a client or other device. It may even be a user setting.

In one embodiment the CCE 120 is configured to set the priority of a user setting to a low priority. The CCE 120 is also configured to set a priority of a TLP resulting from a health status depending on the severity of the health status. The severity of a health status may be stored in a list or provided by an external service provider.

In one embodiment, the priority may be set according to the difference between the ALP and the TLP—a large difference being given a high priority. This allows for users who are so to say far behind to catch up.

In the following there will be made no distinction between adjusting based on the TLP or the difference between the TLP and the ALP, but it should be noted that both are possible and also the combination.

As an example, if a third user, user 3, has an eye problem the severity of his eye problem is most likely higher than the severity of the person having a winter depression. Normally a user suffering from winter depression can withstand (shorter) periods of darker light, whereas a user suffering from an eye problem may not be able to withstand even short periods of bright light. User 3 thus have a TLP3 having a higher priority than the TLP2 of user 2 and the TLP1 of user 1.

The CCE 120 is, in one embodiment, configured to adjust the light in a zone/are according to a weighted average, where the TLPs are weighted according to their priorities. For example if TLP1 has a priority of 5 and TLP2 has a priority of 7 the resulting TLP is:

TLP=5/12*TLP1+7/TLP2.

In an alternative or additional embodiment the CCE 120 is configured to adjust the light in a zone/are according to a TLP having the highest priority.

In a combination of the weighted average and the highest priority scheme, the CCE 120 is configured to determine if a priority has a special priority level and if so, adjust the LCS according to that TLP, and if no special priority exists, then adjust according to a weighted average. If more than one TLP has a special priority, the CCCE 120 may either adjust according to the highest TLP priority or according to a weighted average of the TLPs having a special priority.

To illustrate an example will be given with reference to FIG. 1. User 1 (the moody teenager) is in the living room watching TV. The CCE 120 has adjusted the LS 110b to dim the light according to TLP1. As user 2 walks in to the room, the CCE 120 adjusts the LS 110b to illuminate brighter according to TLP2 having a higher priority.

User 3, who has been working in the working room, also comes in, whereupon the CCE 120 adjusts the LS 110b again to dim the light to save user 3's eyes.

The sensors being worn may be arranged to determine their location explicitly (through for example a Global Positioning System) or through the use of beacons and to communicate their position to the CCE 120 so that the CCE 120 can determine which user is in which zone.

The LS 110 may also be other light sources than lamps and such. For example, motorized blinds could be open or shut to regulate the amount of indirect light coming in. Also indoor tapestry could be used to regulate the reflection given off by special surfaces.

The control of the LS 110 may be dependent on time of day and also the season. For example, opening blinds to increase light has no effect in the middle of the night in most areas.

Also, the control of the LCS 200 may be dependent on the room type. For example, it may be an intrusion on a user's personal integrity to automatically open the blinds in a bed room to increase the light, whereas it may be bad for business to close the blinds in a showroom or business place, for example real estate office.

Alignment of the ALP to the TLP for each individual may also be done in special zones or cubes where the individual can spend time to get a more individually optimized light to quicker compensate the gap and get a quicker alignment between ALP and TLP. The CCE 120 may be configured to communicate to an individual that the current AP is not suitable and that the individual should seek out an individualized zone.

The LCS 200 may also be configured to adapt the ALP according to a room type. For example the wanted light profile of a TV room would differ from the wanted light profile of a working area. In one the light should be dimmed so as not to disturb the TV, whereas in the work area the light should be bright enough to allow for example easy reading. The TLP may in such an embodiment simply state an average light level (or minimum/maximum light level) and not a complete list of settings for each possible environment.

It should be noted that not only the amount of illumination may be adjusted, but also the spectrum of the light. For example if light is needed for a task, but all TLPs indicate that a low light level should be used, the light may be shifted towards the red spectrum as this gives a softer, less intrusive light which is still possible to perform certain tasks in.

In such an embodiment the LCS 200 is arranged to also change its configuration as a room changes purpose or is refitted for example when a certain room/location or part of a room (area) changes objective. One example is when a work room/area is changed to be used for other purposes for example a relaxation room/area or a room for watching a movie. Such changes can happen during different hours of the day or less frequent and such change could he triggered in a multiple different ways for example through a client or a certain timer or just by a wall mounted, hard switch. The LCS 200 will then adopt and adjust the lightening in line with the changed objective/purpose of the room/area.

To set up a LCS a consumer may start out mall and only purchase one or a few lamps which are part of a LCS and one or a few sensors which he carries with him. With a user's client device, for example a phone, he can register to a CLP (a commercial light system provider) if he wishes (but he is not forced to), and download an application to start to operate his own mini-LCS. The mobile phone then operates as a CCE 120 or is configured to operate in cooperation with a remote CCE for example via a telecommunications interface.

It should be noted that a CCE 120 may not necessarily be a server in itself, but may also be a computer software module being executed on a computer, or server, remotely or locally.

Should the user be a registered user with a CLP he might get his own equipment, subsidized by the CLP and also be able to take part of the services as the CLP will provide. The user might choose not to invest in a local server but rather use a cloud server where he has his own CCE. The CCE will start register light input data from the sensors and build up the user's ALP. The TLP is formed by the input data at the registration and is then also gradually updated thru inputs from the sensors and from the user's client, for example it could be from food intake, medical intake, sleep etc.

A client device, such as a smartphone may then be arranged to receive input from a user on his habits and actions and forward the data to the CCE to adjust the TLP or the ALP or adjust the TLP or ALP directly. In one embodiment the smartphone is arranged to prompt the user (regularly or at random times) for input on his habits and actions.

After some time, the user may want to buy more components to his mini-LCS, eg. some more LS of different type as he might install in other rooms. He might still have his CCE in a cloud service, but the CCE will then update the system configuration to the new actual state. The user might fancy the alarm service as the LCS can give and as the CLP will offer, and joins a subscription from the CLP. Now is the CLP also giving the user a possibility to get light treatment at special service places. A gym, for example, is such a place where you can start your day with e.g. a 30 min light treatment. The service is provided thru the subscription. Gradually will the service levels be able to become more and more advanced, see above and the user's system might be built out with more and more advanced LSs and sensors everywhere in the user's home. In a future vision, the LCS will be able to provide advice to individual health improvements thanks to the capabilities in the system where it will be possible for the user to continuously accumulate his health data, food intake and the exposure of light. The quality of light is very important, and the LCS will be able to improve the individual's state of health dramatically.

Figure 2:
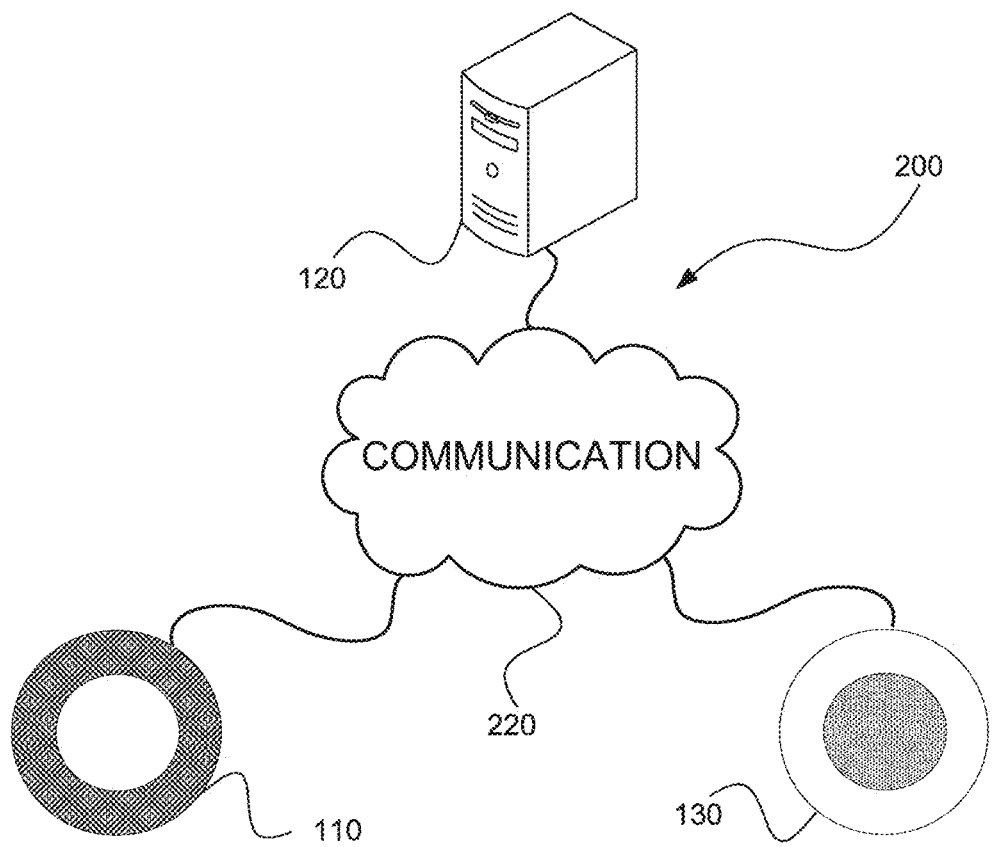
FIG. 2 shows a schematic view of a light control system according to one embodiment of the teachings of this application.

FIG. 2 shows a schematic view of a LCS 200. The LCS 200 comprises a central control engine, CCE 120, one or more light sensors 130, one or more light sources (LS) 110, a database (DB not shown in FIG. 2, but referenced 340 in FIG. 3) for storing user target light profiles (TLP). The CCE 120 may also comprise one or more clients and networks.

Through the networks and clients a distributed control of the LCS may be achieved. Furthermore miscellaneous data which may influence the control may also be gathered. Examples are that if a storm is coming and a user's TLP and ALP indicate a shortage of illumination, the LCS may gather this information from a weather service and increase the brightness to allow for an alignment of the ALP and the TLP before the storm comes.

The light sources, LS 110, can be controlled centrally from the CCE 120, or distributed by any system client, such as a mobile phone, a local computer, or a tablet, or for example by fixed switches or dimmers integrated in the building. The light sources may also be light controlling devices such as blinds, tapestry, curtains or such.

The CCE 120 will at any time register any changes in states of the system components (the light sensors 130 and the light sources 110) and the individuals (such as health status or position) registered in the LCS 200 and adjust the LS 110 accordingly. As stated above the position may be retrieved from the sensors, or from the clients (if they are arranged with position determining means, which most mobile phones are).

The LCS 200 also comprises one or several light sensors 130. The sensors may be arranged on a person to be worn or to be mounted at certain points in an area. The sensors may be arranged to measure the light it is being exposed to and also at which spectra the light is. The sensors 130 may also be arranged to determine a current position and communicate this to the CCE 120 or a client which may forward the information to the CCE 120.

Figure 3:
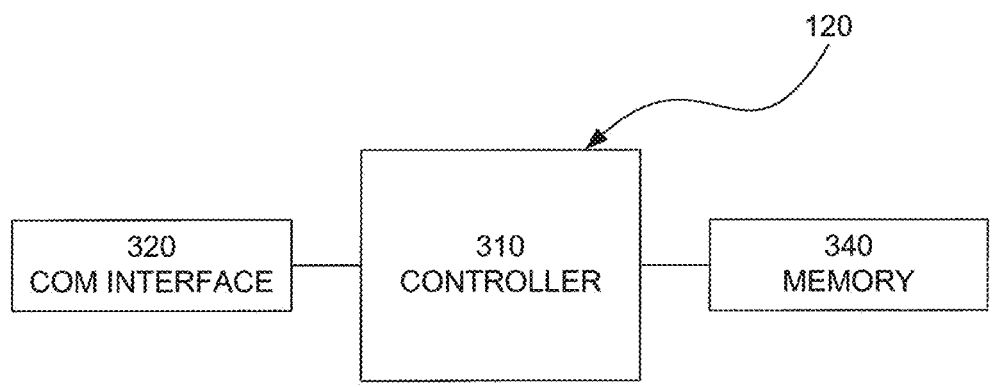
FIG. 3 shows a schematic view of the general structure of a server implementing a central control engine according to one embodiment of the teachings of this application.

FIG. 3 shows a schematic view of the general structure of a computer server implementing a Central Control Engine (CCE) 120 for use in a LCS 200 according to FIG. 2. The CCE 120 comprises a controller 310. The controller 310 may be implemented using instructions that enable hardware functionality, for example, by using executable computer program instructions in a general-purpose or special-purpose processor that may be stored on a computer readable storage medium (disk, memory etc) 340 to be executed by such a processor. The controller 310 is configured to read instructions from the memory 340 and execute these instructions to control the operation of the LCS 200. The memory may be implemented using any commonly known technology for computer-readable memories such as ROM, RAM, SRAM, DRAM, CMOS, FLASH, DDR, SDRAM or some other memory technology.

The memory is also arranged to store at least one TLP for at least one individual associated with the LCS 200.

The CCE 120 further comprises a communication interface 320, such as a radio frequency interface 320, which is adapted to allow the CCE 120 to communicate with LSs 110 through a radio frequency band through the use of different radio frequency technologies. Examples of such technologies are Wife, Bluetooth, W-CDMA, GSM, UTRAN, LTE and NMT to name a few. In one embodiment the communication interface 320 may additionally or alternatively comprise a wired interface.

The CCE 120 may be implemented on a central server in a home or on a CLPs server or as part of a cloud service. Individuals may register to a system to become part of it and thus allow the CCE to give each such registered individual, individually adapted light. Roaming mechanisms may be applied, thus can a guest register into a hosts system. Such registration is then giving the host CCE of the host's LCS knowledge of the guest TLP and ALP and start the service of provide the guest with the appropriate, individualized light.

Clients may be any type of mobile phones, tablets, computers, remote controls etc, and may have individual application SW installed as tool input for the light system control or eg. individual LS in the system. It is assumed that clients can be used for storing and bridging of data transfer from & to the system database.

The system components, eg. the light sources, LS, might have different properties and should be able to report individually to the system about its properties and state. As stated above, the light sources may also be devices for regulating other indirect light sources, such as blinds.

The light sources, LS, will be of different types and some sources will be controllable both for the light direction, amplitude and wavelength while others will have more limited properties. Some light source may also have sensor inbuilt, thus being able to give feedback on the actual transmitted light from the LS as well as the surrounding light. The LS could even have cameras or image sensors inbuilt to give more qualitative feedback to the LCS.

The light sensor will be of different types and could also be part of different personal items, such as wristwatches, glasses, rings, clothing or as "stickers", i.e. being possible to easily stick/glue on. Light sensors will normally also have wireless capability to be able to more easily distribute its data back to the CCE thru the clients or directly thru a home wireless network. Sonic sensors could also be of "self contained" type, they have a solar sensor included, so that they can operate without battery also.

Each component in the LCS, eg. the LSs, each sensor, each client etc will be individually identified and addressable thru the network, which might be consisting of both wireless and wired connections.

The LCS database may be stored locally in the memory 340 or it may be stored remotely at a remote server. The data base may also be part of a cloud service and is thus accessible at many different positions should a user roam from one LCS to another.

If two or more LCSs overlap they may be arranged to cooperate. The cooperation may be necessary to adapt the light setting to different individuals' TLPs and also to prevent oscillations that may arise if both or all) LCSs are trying to lower the light in an area at the same time, whereupon the light will most likely be dimmed too much (as all lights are dimmed at the same time and not only the ones belonging to one LCS, the light sensor of one LCS is not able to distinguish between light from a LS belonging to another LCS and the Light belonging to the same LCS). And as the LCSs want to accommodate for the rapid dimming, the LCSs may all increase the light again resulting in a too fast increase and so on.

To prevent such situations from occurring the LCS 200 may be arranged to cooperate with other LCS 200, possibly through the communication interface 320, for example a telecommunications interface.

The cooperation may be arranged as a distributed control, where all CCEs 120 in the respective LCS 200 control their respective LS 110 but coordinates the control.

In one embodiment the control is coordinated so that the CCEs 120 agrees which LS 110 to be lowered or by how much it may be lowered.

In one embodiment the control is coordinated simply by allowing each CCE 120 to control its own LS 110 but at a weighted rate. In such an embodiment having for example N CCEs 120, each control signal from each CCE 120 is divided by N. This slows down any changes and thus prevents any fast oscillations from occurring.

In one embodiment the CCE 120 may be configured to avoid such problems by setting the LS 110 to a set (absolute) strength and not simply controlling the light to increase/decrease. This requires the LS 110 to be able to determine the illumination level in its surrounding and will adapt the light accordingly.

The cooperation may additionally or alternatively be arranged as a centralized control, where all CCEs 120 in the respective LCS 200 surrender control to one master CCE 120 which sends out control commands to the various CCEs 120 after having received input from the various LCS' sensors 130 and also the TLPs of the individual for each LCS 200.

The CCE 120 chosen as the master may be the CCE of the system having the highest (or most) priority for its registered individuals.

Where the control is both centralized and distributed, the control may be centralized as regards some areas and/or light sources and distributed as regards to some areas and/or light sources.

Another important aspect of the LCS is that it can be part of a traditional communication system. Individuals could initiate different actions or trigger messages or commands through for example gestures and movements. The LCS will be able to detect changes in movements or/and light by for example reflections of light. Such gestures may be interpreted as individual commands, which could either be standardized or individually set. The LCS and a traditional telecom system (for example a cellular based system based on cellular telecom technology such as LTE) may be connected together and thus could messages be transported both ways and handled by both systems separately or even in parallel.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other devices. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

One benefit of the teachings herein is that a user's individual needs are met through a clever and insightful arrangement of light sources and the control thereof based on chosen parameters. And through the use of a priority scheme conflicts between users' differing needs are resolved. Other benefits include that the LCS is useful and provides value to single users also in a small scale and may operate in parallel with existing and also different light sources and light systems.

It is also possible for an operator, a commercial light provider (CLP), which might be an energy company or even a telecommunication service provider, but in general it could be any company interested in providing services, to operate a LCS with multiple users, on a local, regional, national, international or even global scale. The LCS is thus a great complement to today's technology but will thanks to its features and capabilities gradually grow in attraction.

The invention has mainly been described above with reference to a few embodiments. However, as is readily appreciated by a person skilled in the art, other embodiments than the ones disclosed above are equally possible within the scope of the invention, as defined by the appended patent claims.

ABBREVIATIONS

ALP—Actual Light Profile. The accumulated light you have received over time
CCE—Central Control Engine. The central control. Could be SW program.

CLP—Commercial Light Provider. Could be a traditional operator within the energy sector or telecom sector but could be also any other business oriented actor.

IF—Individual Factors. Any relevant factor with some relevant influence from the exposure of light.

LCS—Light Control System. A system independent of specific connecting technology, which could be built from only one LS and later expanded to >millions of LSes. Specified in this document.

LS—Light Source. Eg a LED (Light Emitting Diode) lamp.

ME—Mapping Engine. Comprises of algorithms which the CCE uses to align ALP with TLP.

TLP—Target Light Profile. The preferred accumulated light exposure an individual should have in time.

The invention claimed is:

1. A light control system configured to service more than one individual user, the light control system comprising:
   a central control engine;
   a light sensor; and
   a light source;
   wherein the central control engine is configured to:
     receive illumination data from the light sensor, the illumination data pertaining to an individual user;
     add the received illumination data to an individual actual light profile for the individual user, wherein the individual actual light profile contains first data on an amount of illumination received over time by the individual user, wherein in the first data includes information about at least one of spectrum and intensity;
     retrieve an individual target light profile for the individual user, wherein the individual target light profile contains second data on the amount of illumination to be received by the individual user, wherein the second data includes information about at least one of spectrum and intensity;
     assign a priority to the individual target light profile; wherein the priority is based on a difference between the individual actual light profile and the individual target light profile; and
     adjust an illumination of the light source based on the assigned priority, the individual target light profile and the individual actual light profile.

2. The light control system according to claim 1, wherein the central control engine is further configured to adjust the illumination based on a comparison between the individual target light profile and the individual actual light profile.

3. The light control system according to claim 1, wherein the central control engine is configured to adjust the illumination based on a difference between the individual target light profile and the individual actual light profile.

4. The light control system according to claim 1, wherein the central control engine is configured to continuously receive the illumination data and to continuously add the received illumination data to the individual actual light profile.

5. The light control system according to claim 1, wherein the individual target light profile is adjusted dynamically.

6. The light control system according to claim 1, wherein the individual target light profile is adjusted dynamically based on state of health, food intake, time of the day, sleep history, and/or medical intake of the individual user.

7. The light control system according to claim 1, wherein the central control engine is configured to adjust the individual target light profile based on relationships between the state of health, food intake, time of the day, sleep history, and/or medical intake of the individual user and a desired individual target light profile.

8. The light control system according to claim 1, wherein the individual actual light profile comprises data on what increment or frequency the illumination has been received at.

9. The light control system according to claim 1, wherein the light sensor is associated to the individual user.

10. The light control system according to claim 1, wherein the light sensor is configured to determine a current position of the individual user.

11. The light control system according to claim 10, wherein the central control engine is configured to adjust the illumination based on the current position of the individual user.

12. The light control system according to claim 1, wherein the central control engine is further configured to resolve a conflict between two users each having an individual target light profile by adjusting the illumination based on the individual target light profile and/or a difference between each respective individual target light profile and each respective individual actual light profile of the user having a highest priority.

13. The light control system according to claim 1, wherein the central control engine is further configured to resolve a conflict between two users each having an individual target light profile by determining a weighted average of the individual target light profiles and/or a difference between each respective individual target light profile and each respective individual actual light profile.

14. The light control system according to claim 1, wherein the individual target light profile and/or the individual actual light profile is dependent on race, age, sex and/or health status of the individual user, geographical location, season, weather, weather reports, and/or preference of the individual user.

15. A method for controlling a light source, the method comprising:
   receiving illumination data from a light sensor, the illumination data pertaining to an individual user;
   adding the received illumination data to an individual actual light profile for the individual user, wherein the individual actual light profile contains first data on the amount of illumination received by the individual user, wherein the first data includes information on at least one of spectrum and intensity;
   retrieving an individual target light profile for the individual user, wherein the individual target light profile contains second data on the amount of illumination to be received by the individual user, wherein the second data includes information on at least one of spectrum and intensity;
   assigning a priority to the individual target light profile, wherein the priority is based on a difference between the individual actual light profile and the individual target light profile; and
   adjusting an illumination of the light source based on the individual target light profile and the individual actual light profile.

16. The light control system according to claim 1, wherein the individual target light profile comprises third data of at least one of an increment and the frequency the illumination should be received.

17. A light control system configured to service more than one individual user, the light control system comprising:
   a central control engine;
   a light sensor; and
   a light source;
   wherein the central control engine is configured to:

receive illumination data from the light sensor, the illumination data pertaining to an individual user;

add the received illumination data to an individual actual light profile for the individual user, wherein the individual actual light profile contains first data on an amount of illumination received over time by the individual user, wherein the first data includes information about at least one of spectrum and intensity;

retrieve an individual target light profile for the individual user, wherein the individual target light profile contains second data on the amount of illumination to be received by the individual user, wherein the second data includes information about at least one of spectrum and intensity;

assign a priority to the individual target light profile, wherein the priority is based on a health status; and adjust an illumination of the light source based on the assigned priority, the individual target light profile, and the individual actual light profile.

18. A method for controlling a light source, the method comprising:

receiving illumination data from a light sensor, the illumination data pertaining to an individual user;

adding the received illumination data to an individual actual light profile for the individual user, wherein the individual actual light profile contains first data on the amount of illumination received by the individual user, wherein the first data includes information on at least one of spectrum and intensity;

receiving an individual target light profile for the individual user, wherein the individual target light profile contains second data on the amount of illumination to be received by the individual user, wherein the second data includes information on at least one of spectrum and intensity;

assigning a priority to the individual target light profile, wherein the priority is based on a health status; and adjusting an illumination of the light source based on the assigned priority, the individual target light profile, and the individual actual light profile.

* * * * *